(12) United States Patent
Chin et al.

(10) Patent No.: US 7,766,816 B2
(45) Date of Patent: Aug. 3, 2010

(54) METHOD AND APPARATUS FOR CLOSING OFF A PORTION OF A HEART VENTRICLE

(75) Inventors: Sing-Fatt Chin, Pleasanton, CA (US); Lon Annest, Tacoma, WA (US)

(73) Assignee: CHF Technologies, Inc., San Ramon, CA (US)

( * ) Notice: Subject to any disclaimer, the term of this patent is extended or adjusted under 35 U.S.C. 154(b) by 763 days.

(21) Appl. No.: 11/450,131

(22) Filed: Jun. 8, 2006

(65) Prior Publication Data

US 2007/0049971 A1 Mar. 1, 2007

Related U.S. Application Data

(60) Provisional application No. 60/689,012, filed on Jun. 9, 2005.

(51) Int. Cl.
*A61F 2/00* (2006.01)
(52) U.S. Cl. .................................................. 600/37
(58) Field of Classification Search ............ 600/16–18, 600/29, 32, 37; 128/897–899
See application file for complete search history.

(56) References Cited

U.S. PATENT DOCUMENTS

| 5,295,958 | A | 3/1994 | Shturman |
|---|---|---|---|
| 5,961,440 | A | 10/1999 | Schweich, Jr. et al. |
| 6,050,936 | A | 4/2000 | Schweich, Jr. et al. |
| 6,059,715 | A | 5/2000 | Schweich, Jr. et al. |
| 6,125,852 | A | 10/2000 | Stevens et al. |
| 6,165,119 | A | 12/2000 | Schweich, Jr. et al. |
| 6,260,552 | B1 | 7/2001 | Mortier et al. |
| 6,406,420 | B1 | 6/2002 | McCarthy et al. |
| 6,616,684 | B1 * | 9/2003 | Vidlund et al. ............... 606/213 |
| 6,746,471 | B2 | 6/2004 | Mortier et al. |
| 6,776,754 | B1 | 8/2004 | Wilk |
| 2002/0077524 | A1 | 6/2002 | Schweich, Jr. et al. |
| 2002/0169359 | A1 | 11/2002 | McCarthy et al. |
| 2003/0166992 | A1 | 9/2003 | Schweich, Jr. et al. |
| 2004/0225304 | A1 | 11/2004 | Vidlund et al. |
| 2005/0096498 | A1 * | 5/2005 | Houser et al. .................. 600/37 |
| 2006/0247672 | A1 | 11/2006 | Vidlund et al. |
| 2007/0049971 | A1 | 3/2007 | Chin et al. |

OTHER PUBLICATIONS

International Search Report and Written Opinion of PCT Application No. PCT/US06/22594, dated Oct. 1, 2008, 9 pages total.

\* cited by examiner

*Primary Examiner*—Charles A Marmor, II
*Assistant Examiner*—Christine D Hopkins
(74) *Attorney, Agent, or Firm*—Townsend and Townsend and Crew LLP

(57) ABSTRACT

Apparatus and methods to reduce ventricular volume are disclosed. The device takes the form of a transventricular anchor, which presses a portion of the ventricular wall inward, thereby reducing the available volume of the ventricle. The anchor is deployed using a curved introducer that may be inserted into one ventricle, through the septum and into the opposite ventricle. Barbs or protrusions along the anchor body combined with a mechanical stop and a sealing member hold the device in place once deployed.

25 Claims, 3 Drawing Sheets

METHOD AND APPARATUS FOR CLOSING OFF A PORTION OF A HEART VENTRICLE

CROSS REFERENCE TO OTHER APPLICATIONS

This application claims the benefit of U.S. provisional application Ser. No. 60/689,012 filed Jun. 9, 2005, the disclosure of which is hereby incorporated by reference in its entirety.

FIELD OF THE INVENTION

The present invention relates to methods and apparatus for temporarily or permanently closing off a portion of the ventricle of the heart.

BACKGROUND OF THE INVENTION

In left ventricular hypertrophy, the myocardium of the left ventricle becomes thickened to the point of interfering with effective heart contraction. A surgical procedure for treating congestive heart failure, involves removing a triangular portion of a patient's heart. In this operation, approximately one-third of the patient's left ventricular muscle is removed. The result is that the smaller heart pumps more efficiently. This new technique of course requires open-heart surgery, with its attendant expense and extended convalescence.

One method to reduce ventricular volume is disclosed in U.S. Pat. No. 6,776,754 to Wilk, which is hereby incorporated by reference in its entirety.

For this and other potential procedures, it would be beneficial to have a method and system that could be temporarily and/or permanently implanted to close off a portion of the ventricle.

SUMMARY OF THE INVENTION

The present invention relates to a catheter or surgical based system capable of closing off a portion of a ventricle of a patient. The ventricle may be temporarily blocked during a surgical procedure or it may be permanently or semi-permanently closed off to improve cardiac function.

The present invention takes the form of an anchor for performing heart reconstruction including an elongated body, a plurality of protrusions extending from the body, and first and second mechanical stops or sealing members attachable to the body.

The anchor of mechanical stop may include two or more folding arms. The folding arms may be pivotally attached to the first end of the body.

One end of the anchor may include a curved needle that forms one end of the anchor.

The anchor may be used with a curved introducer. The elongated body being sized and configured to pass through the curved introducer.

The second sealing member may be held in place by a plurality of protrusions.

The sealing member may be formed of a resilient material.

A method of performing ventricular reconstruction, including the steps: (a) passing a curved needle through an anterior wall of a left ventricle of a patient; (b) passing the curved needle through the septum and into the right ventricle; (c) inserting an anchor into the needle; (d) allowing one or more arms located on a distal end of said anchor to deploy; (e) removing the curved needle; (f) placing a sealing member over a proximal end of said anchor; (g) folding a wall of the ventricle inward; (h) and using the sealing member to hold the folded wall in place.

The method may include passing the curved needle through an anterior wall of the right ventricle prior to step (d).

The method may be used to reduce the volume of the left ventricle and/or to treat left ventricular hypertrophy.

The method may include using the sealing member to hold the wall of the ventricle in place by engaging one or more protrusions extending from the anchor.

The method using a sealing member formed of a resilient material, such that the sealing member is resiliently deformed, thereby resiliently pressing against the wall of the ventricle.

The method may include the step of removing a portion of the anchor after the wall of the ventricle has been moved.

The method may be used to temporarily or permanently implant the device.

DETAILED DESCRIPTION

Figure 1A:
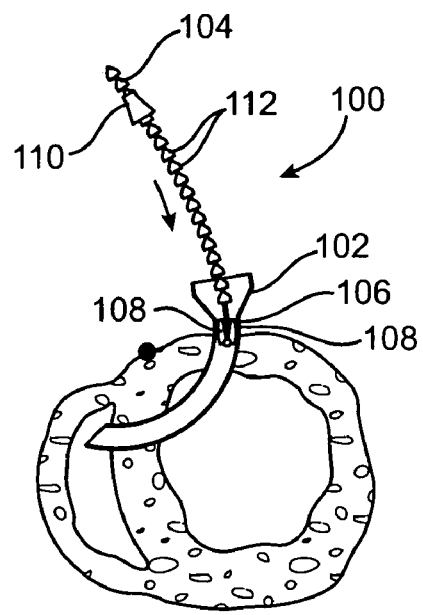
FIGS. 1A-1C show a method and device for left ventricular reconstruction using a left ventricular approach.
Figure 1B:
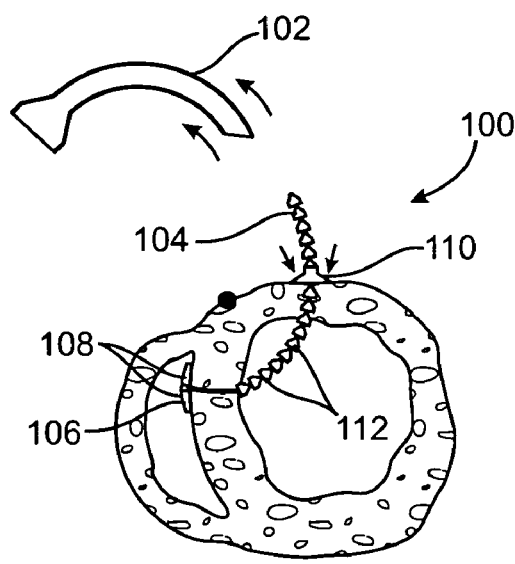
Figure 1C:
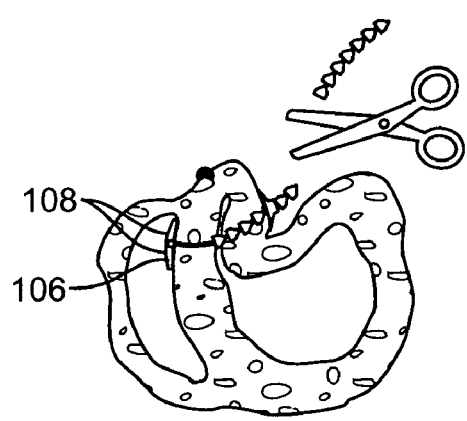

FIGS. 1A-1C show a method and device 100 for left ventricular reconstruction using a left ventricular approach. The device is an anchor deployment system 100, which is guided to the correct location on the heart by introducing a hollow curved introducer or needle 102 in through the anterior wall of the left ventricle. A visual guidance system, such as TEE, may be used to ensure the placement accuracy. The tip of the curved needle 102 is then guided through the septum and into the right ventricle. Either before placement or once the needle 102 is in place, the transventricular anchor 104 is loaded into the needle 102. The distal tip of the anchor 104 is extended into the cavity of the right ventricle.

The distal tip of the anchor 104 has a mechanical stop 106. Although it may take any suitable form, such as a resilient member or mechanical device, in the embodiment shown, the stop 106 has two or more pivoting arms 108. While the anchor 104 is within the needle 102, the arms 108 are held close to the body of the anchor 104. When the distal tip of the anchor 104 extends beyond the distal tip of the needle 102, the arms 108 are free to open. The arms 108 may be biased toward the open position or they maybe be manually opened. Once opened, the arms 108 prevent the distal end of the anchor 104 from passing back through the opening in the septum.

After the anchor 104 is in place, the needle 102 may be removed. A proximal sealing lock 110 is then slid onto the proximal end of the anchor 104. The sealing lock 110 is slid along the body and over one or more barbs 112 or other protrusions extending from the body of the anchor 104. The barbs 112 may take any suitable form, such as rounded or triangular. In the embodiment shown, the barbs 112 are generally triangular in shape. The proximal sealing lock 110 is advance until the anterior wall of the left ventricle is pressed inward, thereby folding the wall and reducing the interior volume of the left ventricle. Once the sealing lock 110 is advanced into place, the proximal portion of the body of the anchor 104 may be trimmed or cut off. Although the sealing lock 110 may be formed of any suitable material, the sealing lock 110 shown is made of a resilient material to allow it open and be compressed against the heart tissue. The resilience of the material provides benefits both in helping to seal the opening created as well has resiliently holding the wall of the ventricle in the modified configuration.

In alternate embodiments, an adhesive, bonding or other mechanical or chemical means may be used to connect the sealing lock 110 to the anchor 104.

If desired, the tip of the hollow needle 102 may be equipped with a pressure sensor to guide the practitioner to know if the tip is in the left ventricle, septum or the right ventricle by sensing the pressure. The hollow needle 102 may also be equipped with electrical sensor (EKG, Monophasic Action Potential) to sense if the puncture sight is the viable tissue or infarcted tissue.

Figure 2A:
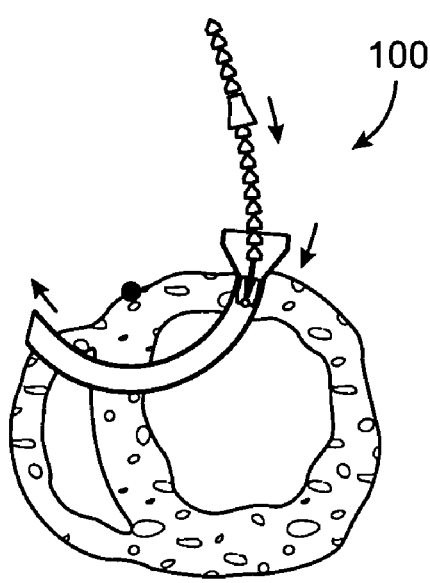
FIGS. 2A-C show an alternate procedure of FIGS. 1A-C.
Figure 2B:
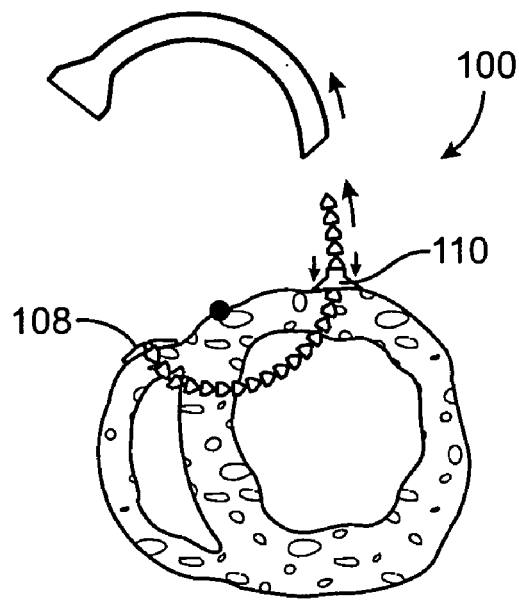
Figure 2C:
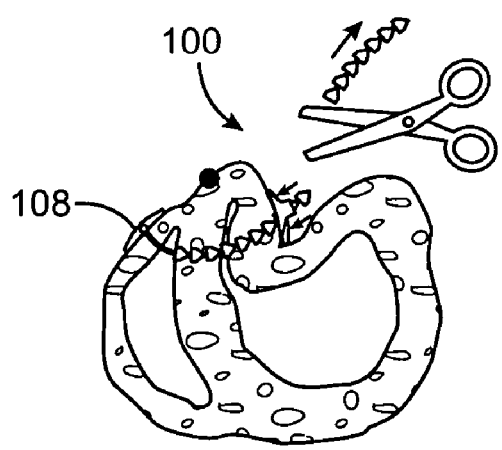

FIGS. 2A-C show an alternate procedure of that shown in FIGS. 1A-C. In this method, the distal end of the anchor is again guided to the anterior wall of the left ventricle. The tip of the curved needle 102 is then guided through the septum and into the right ventricle. In the configuration shown in FIG. 2A, the introducer 102 also extends through the anterior wall of the right ventricle. Once deployed, the distal tip of the anchor 104 is outside the right ventricle and the proximal tip is outside the left ventricle.

Figure 3A:
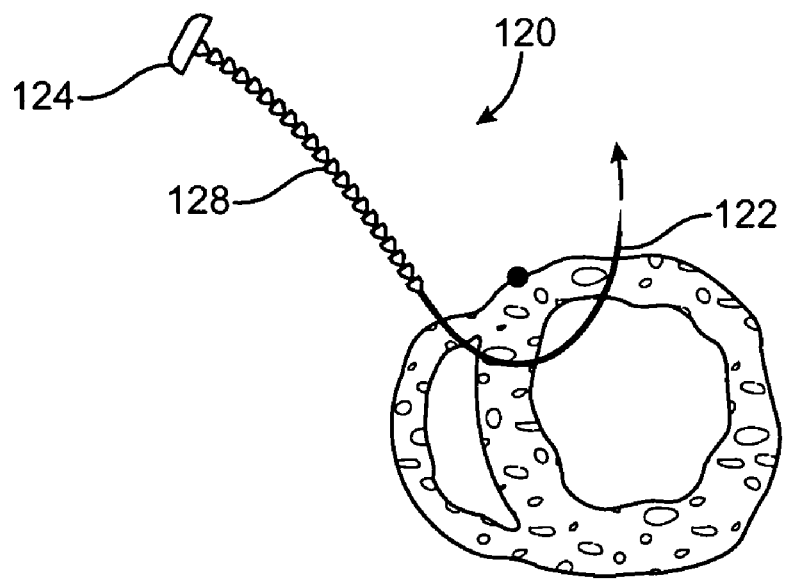
FIGS. 3A-B show a method and device for left ventricular reconstruction using a right ventricular approach.
Figure 3B:
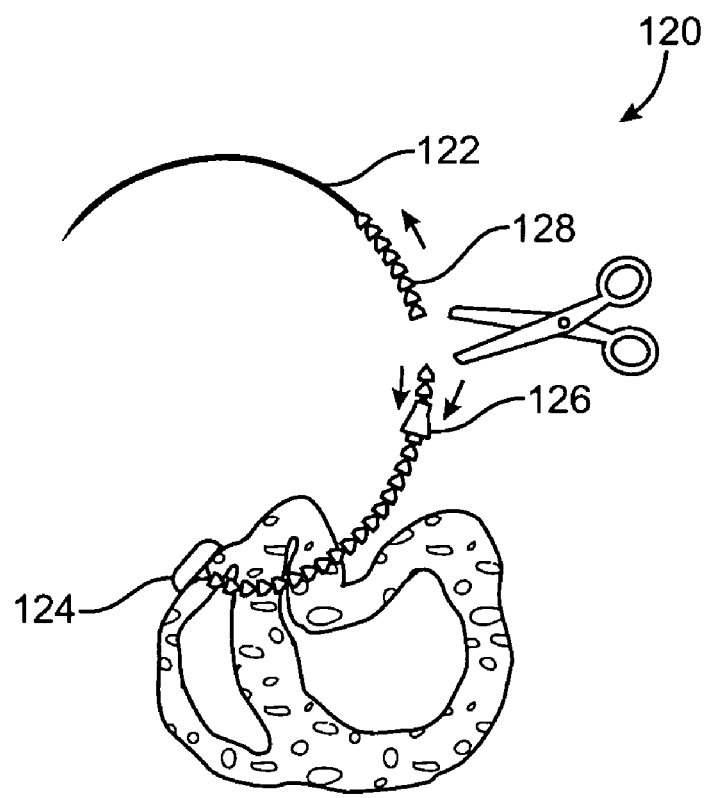

FIGS. 3A-B show a method and device for left ventricular reconstruction 120 using a right ventricular approach. In this version, a curved needle 122 forms the distal tip of the anchor. The curved needle 122 is inserted through the anterior wall and into the right ventricle, through the septum, and through the anterior wall of the left ventricle. The body of the anchor follows the curved needle 122 and is fed through until the proximal stop 124 engages the anterior surface of the right ventricle. The anterior wall of the left ventricle is pressed inward over the body of the anchor. A distal sealing stop 126 is threaded over the anchor 120 and slid in place against the anterior surface of the right ventricle. The heart tissue may be pressed inward to fold the wall of the heart prior to the placement of the sealing stop 126 or the sealing stop 126 may be used to manipulate the heart tissue. A plurality of barbs or protrusions 128 extend from the surface of the anchor body. The barbs 128 help hold the heart tissue in place. The curved needle 122 and the excess portion of the distal end of the anchor may be removed. This may be done before or after the distal sealing stop 126 has been placed.

The transventricular anchor may be temporarily or permanently implanted. A temporary implantation may be beneficial to test the effectiveness of the treatment for a particular patient. Other surgical procedures may only require a temporary reduction in ventricle volume. For these situations, the device may be removable. To remove the device, it may be cut or broken or another release mechanism may be used to allow for removal of the device. Once the efficacy is confirmed for a patient, a permanent version of the anchor could be implanted. Alternately, a semi-permanent or permanent device may be implanted initially.

The transventricular anchor may be used to treat medical conditions including left ventricular hypertrophy. While the examples given are specific to performance of reconfiguration of the left ventricle. Other procedures could also be performed to reduce the internal volume of other bodily structures, including other chambers of the heart, gastric system, etc.

The present invention may be deployed during an open-heart procedure or it may be done using minimally invasive techniques using catheter systems and/or ports formed between the ribs.

Many features have been listed with particular configurations, options, and embodiments. Any one or more of the features described may be added to or combined with any of the other embodiments or other standard devices to create alternate combinations and embodiments.

Although the invention has been fully described above, in relation to various exemplary embodiments, various additions or other changes may be made to the described embodiments without departing from the scope of the present invention. Thus, the foregoing description has been provided for exemplary purposes only and should not be interpreted to limit the scope of the invention.

What is claimed is:

1. A method of performing ventricular reconstruction of a heart, the method comprising the steps of:
   (a) passing a curved needle from outside the heart through an anterior wall of a left ventricle of a patient to form a perforation of the anterior wall, the curved needle having a curvature;
   (b) passing the curved needle from the perforation of the anterior wall through the septum and into the right ventricle to form a perforation of the septum, the perforation of the septum being offset from the perforation of the perforation of the anterior wall corresponding with the curvature of the curved needle;
   (c) inserting a distal end of an anchor through the perforation of the anterior wall and through the perforation of the septum formed by the needle;
   (d) allowing one or more arms located on the distal end of said anchor to deploy while an elongate proximal end of the anchor extends through the perforation of the anterior wall and through the perforation of the septum;
   (e) removing the curved needle;
   (f) placing a sealing member over the proximal end of said anchor;
   (g) folding a wall of the ventricle inward; and
   (h) holding the folded wall in place using the sealing member so that the anterior wall sealingly engages the septum along the fold and a portion of the ventricle is closed off.

2. The method of claim 1, further comprising the step of passing the curved needle through an anterior wall of the right ventricle prior to step (d).

3. The method of claim 1, wherein (g) folding the wall of the ventricle inward and (h) holding the folded wall in place reduces the volume of the left ventricle.

4. The method of claim 1, wherein the ventricular reconstruction is performed to treat left ventricular hypertrophy.

5. The method of claim 1, wherein the sealing member holds the anterior wall in place by engaging one or more protrusions extending from the elongate proximal end of the anchor.

6. The method of claim 1, wherein the sealing member comprises a resilient material adapted to resiliently press against the wall of the ventricle.

7. The method of claim 1, further comprising removing a portion of the elongate proximal end of the anchor after the step of (g) folding the wall of the ventricle inward.

8. The method of claim 1, wherein the anchor is temporarily implanted.

9. The method of claim 1, wherein the anchor is permanently implanted.

10. The method of claim 1, wherein the one or more arms are pivotally deployed.

11. The method of claim 1, wherein the curved needle comprises a hollow bore and the step of (c) inserting the distal end of the anchor through perforation of the anterior wall and through the perforation of the septum formed by the needle comprises inserting the distal end of the anchor into the hollow bore of the curved needle.

12. The method of claim 1 further comprising passing the curved needle through an anterior wall of the right ventricle to form a perforation of the right ventricular anterior wall.

13. The method of claim 12, wherein inserting the anchor through the perforation of the left ventricular anterior wall and through the perforation of the septum comprises inserting the anchor through the perforation of the right ventricular anterior wall, through the perforation of the septum, and through the perforation of the left ventricular anterior wall.

14. The method of claim 1, further comprising sensing pressure near a tip of the curved needle during the passing of the curved needle so as to determine if the tip is disposed in a ventricle.

15. The method of claim 1, further comprising guiding the passing of the curved needle with reference to echographic images.

16. A method of performing ventricular reconstruction of a heart, the method comprising:
   passing a curved needle from outside the heart through an anterior wall of the left ventricle to form a perforation of the left ventricular anterior wall, the curved needle having a curvature;
   passing the curved needle from the perforation of the anterior wall through the septum and into the right ventricle to form a perforation of the septum, the perforation of the septum being offset from the perforation of the anterior wall corresponding with the curvature of the curved needle;
   inserting an anchor through the perforation of the left ventricular anterior wall and through the perforation of the septum;
   allowing one or more arms of the anchor to deploy while an elongate end of the anchor extends through the perforation of the anterior wall and through the perforation of the septum;
   removing the curved needle;
   placing a sealing member over the elongate end of the anchor;
   folding a wall of the left ventricle inward; and
   holding the folded wall in place using the sealing member so that the anterior wall sealingly engages the septum along the fold and a portion of the left ventricle is closed off.

17. The method of claim 16, wherein the curved needle is coupled to a distal end of the anchor.

18. The method of claim 17, wherein inserting the anchor through the perforation of the left ventricular anterior wall and through the perforation of the septum comprises inserting the distal end of the anchor through the perforation of the left ventricular anterior wall and through the perforation of the septum.

19. The method of claim 17, wherein removing the curved needle comprises removing the curved needle from the distal end of the anchor.

20. The method of claim 16, wherein the elongate end of the anchor comprises an elongate proximal end of the anchor, and the one or more arms of the anchor are disposed on the proximal end.

21. The method of claim 16, wherein placing the sealing member over the anchor comprises placing the sealing member over a distal end of the anchor.

22. The method of claim 16, further comprising removing a portion of the elongate end of the anchor after folding the wall of the ventricle inward.

23. The method of claim 16, wherein the one or more arms are pivotally deployed.

24. The method of claim 16, further comprising sensing pressure near a tip of the curved needle during the passing of the curved needle so as to determine if the tip is disposed in a ventricle.

25. The method of claim 16, further comprising guiding the passing of the curved needle with reference to echographic images.

\* \* \* \* \*